(12) United States Patent  
Walker et al.

(10) Patent No.: US 6,515,748 B2
(45) Date of Patent: Feb. 4, 2003

(54) METHOD AND APPARATUS FOR IN-SITU SPECTROSCOPIC ANALYSIS

(75) Inventors: Dwight Sherod Walker, Durham, NC (US); Lee A Barger, Cary, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/141,741

(22) Filed: May 9, 2002

(65) Prior Publication Data

US 2002/0154309 A1 Oct. 24, 2002

Related U.S. Application Data

(63) Continuation of application No. 09/558,680, filed on Apr. 26, 2000, now abandoned.

(51) Int. Cl.[7] .............................................. G01N 21/00
(52) U.S. Cl. ........................ 356/436; 356/246; 356/440; 250/576
(58) Field of Search ................................ 356/432, 436, 356/440, 244, 246; 250/573, 576, 227.11, 339.12, 227.25; 385/12, 125

(56) References Cited

U.S. PATENT DOCUMENTS

| | | | |
|---|---|---|---|
| 4,013,413 A | 3/1977 | Stewart et al. | |
| 4,264,814 A | 4/1981 | Freund et al. | 250/304 |
| 4,988,155 A | 1/1991 | Harner et al. | 356/246 |
| 5,044,755 A | 9/1991 | Landa et al. | |
| 5,046,854 A | 9/1991 | Weller et al. | 356/440 |
| 5,168,367 A | 12/1992 | O'Rourke et al. | 356/246 |
| 5,268,736 A | 12/1993 | Prather | 356/246 |
| 5,389,524 A | 2/1995 | Larsen et al. | 435/29 |
| 5,407,638 A | 4/1995 | Wang | 422/82.09 |
| 5,442,437 A | 8/1995 | Davidson | 356/246 |
| 5,444,807 A | 8/1995 | Liu | 385/12 |
| 5,452,082 A | 9/1995 | Sanger et al. | 356/246 |
| 5,630,987 A | 5/1997 | Briggs et al. | 422/82 |
| 5,681,749 A | 10/1997 | Ramamoorthy | 436/55 |
| 6,061,139 A | 5/2000 | Takezawa et al. | 356/407 |
| 6,108,083 A | 8/2000 | Machler | 356/328 |

*Primary Examiner*—Hoa Q. Pham
(74) *Attorney, Agent, or Firm*—Charles E. Dadswell

(57) ABSTRACT

An apparatus for in-situ spectroscopic analysis comprising a flow cell having a region of reasonable flow, the region of reasonable flow having a flow rate less than approximately 20% of the maximum flow rate, and first and second probes having optic cable member ends with a path length in the range of 20 $\mu$m to 1 mm that are disposed in the region of reasonable flow.

8 Claims, 7 Drawing Sheets

FIG.—4

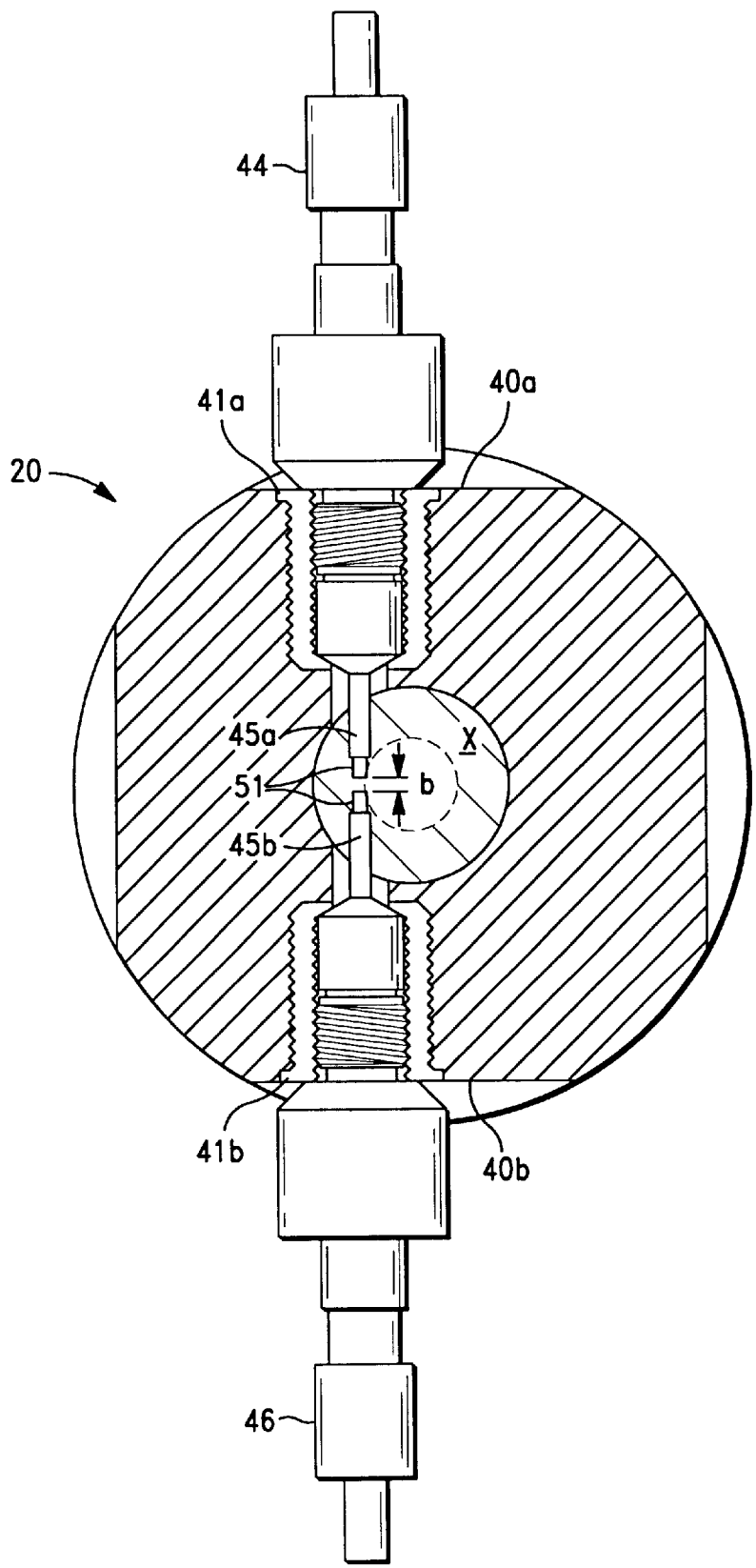
FIG.−8

METHOD AND APPARATUS FOR IN-SITU SPECTROSCOPIC ANALYSIS

This application is filed pursuant to 37 CFR 1.53(b) as a continuation patent application Ser. No. 09/558,680 filed Apr. 26, 2000 now abandoned, in the United States Patent and Trademark Office.

FIELD OF THE PRESENT INVENTION

The present invention relates to on-line spectroscopy systems. More particularly, the present invention relates to a fiber-optic based system for on-line spectral analysis of fluids and other substances.

BACKGROUND OF THE INVENTION

It is well known that the absorption of light by a fluid or other substance (i.e., sample), as a function of wavelength, forms the basis of spectroscopic analysis. The analysis can take place in a number of spectral ranges, ranging from the ultraviolet and visible range where molecules absorb light due to electronic transitions, to the infra-red range where light absorption corresponds to vibrational transitions. In the near infra-red (NIR) region, absorption corresponds to vibrational transitions in the bonds between hydrogen atoms and the rest of the molecule (referred to as X—H bonds).

The exact wavelength at which these X—H bonds adsorb light depends on the structure of the molecule. This forms the basis of NMR analysis, as different molecules, such as aromatics, aliphatics and olefins, have different absorption spectra.

A number of devices have been, and continue to be, employed for spectral analysis of samples. The devices are typically employed to measure the reflection, transmission, fluorescence or the light scattering from "on-line" samples.

The "on-line" devices typically comprise three parts: (i) an analyzer, which includes a light or other radiation source and a detection system, (ii) an optical probe for transmitting the light or other radiation to and receiving it from the analyzed sample and (iii) suitable optical fibers for guiding the light or other radiation between the analyzer and the probe. Illustrative is the device manufactured and distributed by the Perkin Elmer Corp.

The Perkin Elmer device includes a probe member (or head) capable of measuring the absolute transmission signal of the sample. The probe includes dual cells, one of which is for sample analysis while the other is a dummy reference cell. The device also includes a mechanical shutter to alternately block and unblock the sample and reference optical paths.

The Perkin Elmer device suffers from a number of disadvantages. First, the probe is made up of many optical components, such as lenses, a beam splitter, prisms, optical windows, and the like, which make it awkward, expensive and difficult to properly align. Second, the probe is inefficient in that at least ¾ of the signal is lost in the course of the double pass through the beam splitter, which is used to split the beam to the reference and sample optical paths.

A further optic-based system is disclosed in U.S. Pat. No. 5,044,755 (I. Landa, et al.). In this system, the light emerging from a fiber bundle is collimated by a lens. The optical ray is then guided through a sample cell and reflected back to the same lens which focuses the light into the same fiber bundle. Some of the fibers are used to guide the light into the transmission probe while some of the fibers are used to guide the light out to the detection system (i.e., analyzer).

Optic-based systems distributed by UOP Guided Wave Inc. and Galileo Electro-Optics Corp. similarly employ a transmission probe in which the light emerging from the fiber, whether a single fiber or a fiber bundle, is collimated by a lens that guides the light through the sample cell. On emerging from the sample cell, the ray is collected by another lens which focuses the optical ray onto a second output fiber.

Finally, in U.S. Pat. No. 5,442,437 (T. Davidson) a flow cell and optic probe assembly is disclosed wherein one probe directs light into the cell chamber and a second probe collects the emitted light. The lens that is typically employed in conventional systems is thus eliminated.

A major drawback of the noted optic-based systems is that the spacing between the optic probe members (i.e., path length) generally cannot be controlled to a satisfactory level. Since the amount of light absorption (i.e., absorbance) is directly proportional to the path length of light passing through the sample being analyzed, the path length must be closely controlled.

A further drawback of conventional optic-based systems is that they typically exhibit either a path length in the range of 0.1 $\mu$m to 1.0 $\mu$m or a path length >1.0 mm. Thus, as discussed in detail herein, since absorbance (A) varies with the wavelength of the absorbing material in direct proportion to the path length (i.e., the absortivity and concentration of the absorbing material held constant), it will be appreciated that conventional optic-based systems have limited applicability.

An additional problem associated with conventional optic-based systems is that the probes tend to become clouded or contaminated when positioned in the flow path of the material to be analyzed (i.e., sample flow path). The design of several probes also make them susceptible to erosion and catastrophic failure (e.g., tip fracture) when exposed to the sample flow path for an extended period of time.

It is therefore an object of the present invention to provide a sample flow cell and fiber-optic probe system that overcomes the above-discussed deficiencies with conventional optic-based spectroscopy systems.

It is another object of the present invention to provide a sample flow cell and fiber-optic probe system that positions the probe members directly in the sample flow path with minimal risk of fracture.

It is another object of the present invention to provide an on-line sample flow cell and fiber-optic probe system having means for accurate control of the path length.

It is yet another object of the present invention to provide a sample flow cell and fiber-optic probe system that includes efficient means of minimizing contamination and clouding of the probe members when positioned in the sample flow path.

SUMMARY OF THE INVENTION

In accordance with the above objects and those that will be mentioned and will become apparent below, the sample flow cell and probe apparatus in accordance with this invention comprises a flow cell having a flow passage and means for introducing a flowable material into the flow passage for flowing therethrough, the flow cell includes a cell chamber in communication with the flow passage, the cell chamber including a region of reasonable flow, a first probe for transmitting light of a given wavelength into the cell chamber, the first probe including a first optic cable member having first and second ends, the first end being disposed in the region of reasonable flow; a second probe for detecting emission light from the flowable material, the second probe including a second optic cable member having first and second ends, the first end being disposed in the region of reasonable flow; the first and second probes having a path length in the range of approximately 20 μm to 1 mm; and control means in communication with the second ends of the first and second optic cable members for providing the light to the first end of the first optic cable member and analyzing the emission light detected by the first end of the second optic cable member.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 7 and 8 are partial section plan views of the sample flow cell and probe apparatus according to the invention.

DETAILED DESCRIPTION OF THE PREFERRED EMBODIMENT

The sample flow cell and probe apparatus of the present invention substantially reduces or eliminates the drawbacks and shortcomings associated with prior art optic-based spectroscopy systems. The apparatus generally includes a first optic member adapted to provide excitation light to a flowable material (i.e., sample), a second optic member adapted to detect the emission light from the sample and control means having light source means for providing the desired wavelength of light and analyzer means for analyzing the emission light. As discussed in detail below, several key features of the apparatus are the unique path length employed, the means of accurately controlling the path length and means for minimizing damage to the optic members when exposed to the sample flow path.

Figure 1:
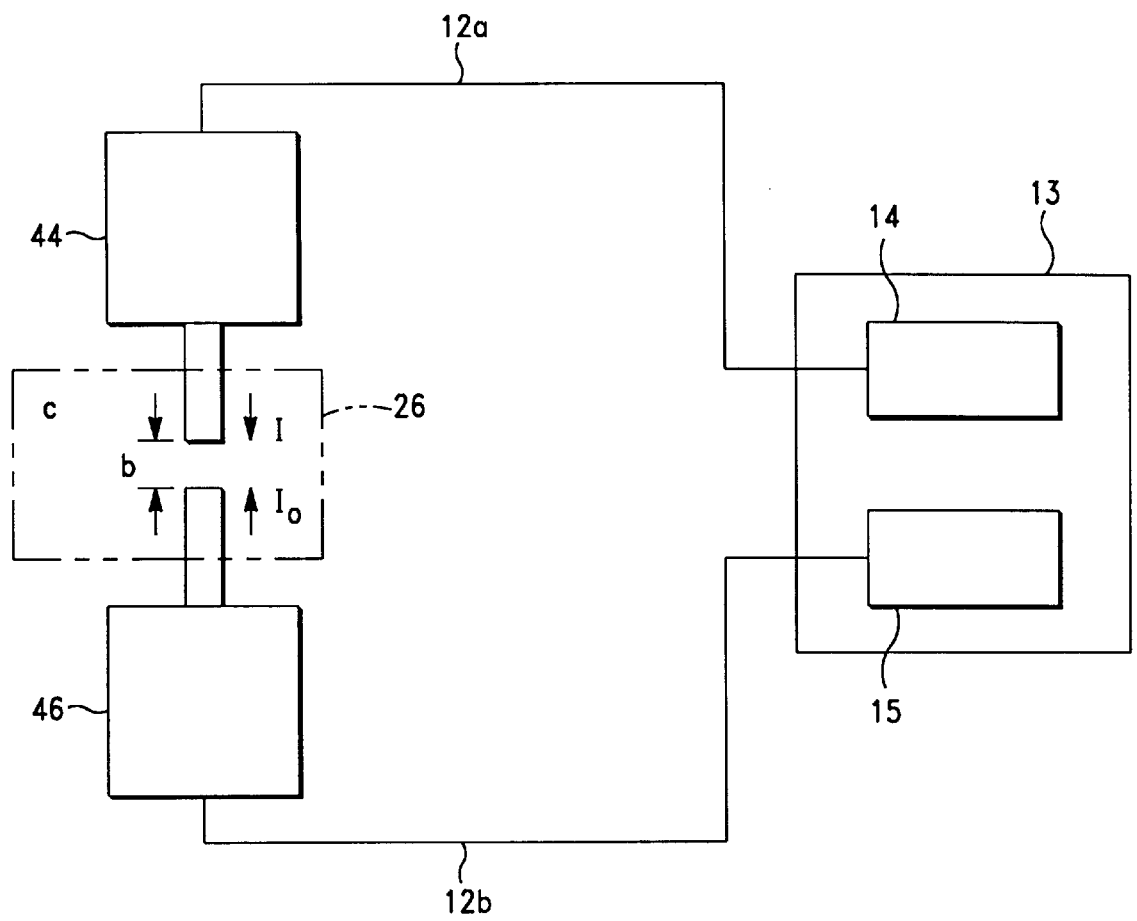
FIG. 1 is a schematic illustration of the optic-based spectroscopic means according to the invention.

Referring first to FIG. 1, there is shown a schematic illustration of the optic-based spectroscopic means of the invention. The spectroscopic means generally comprises a first optic member 44 (or first probe) adapted to provide the excitation light to the sample in the cell chamber (shown in phantom and designated generally 26), a second optic member 46 (or second probe) for detecting the emission light from the sample and control means 13. As illustrated in FIG. 1, the control means 13 includes a light source 14 for providing the desired wavelength of light to the first optic member 44 via line 12a and an analyzer 15 for analyzing the light detected by the second optic member 46, which is communicated to the analyzer 15 via line 12b.

It is well established that when a light absorbing component (i.e., sample) passes through flow cell chamber 26, the amount of light transmitted through the chamber 26 decreases in accordance with Beer's Law, i.e., $$A = \frac{I}{I_0} = 10^{-\alpha bc} \qquad \text{Eq. 1}$$

where:
A=Absorbance
I=Power of transmitted radiation
$I_o$=Power of incident radiation
 =Molar absortivity of the sample
c=Sample concentration (moles/liter)
b=Path length of the light in the chamber (cm.)

The control means output, discussed below, is thus preferably in terms of absorbance (A), which, as shown above, is defined as the product of bc and is proportional to both the sample concentration (c) and path length (b). Generally, conventional optic-based systems exhibit a path length in the range of 0.1 μm to 1.0 μm or a path length >1.0 mm.

In contrast to the noted conventional optic-based systems, the unique spectroscopic means of the present invention employs first and second optic members 44, 46 having a preferred path length in the range of approximately 1 μm to 10 mm, more preferably, in the range of 20 μm to 1.0 mm. As will be appreciated by one having ordinary skill in the art, the noted path length range provides a range of applicability that is unparalleled in the art.

Figure 2:
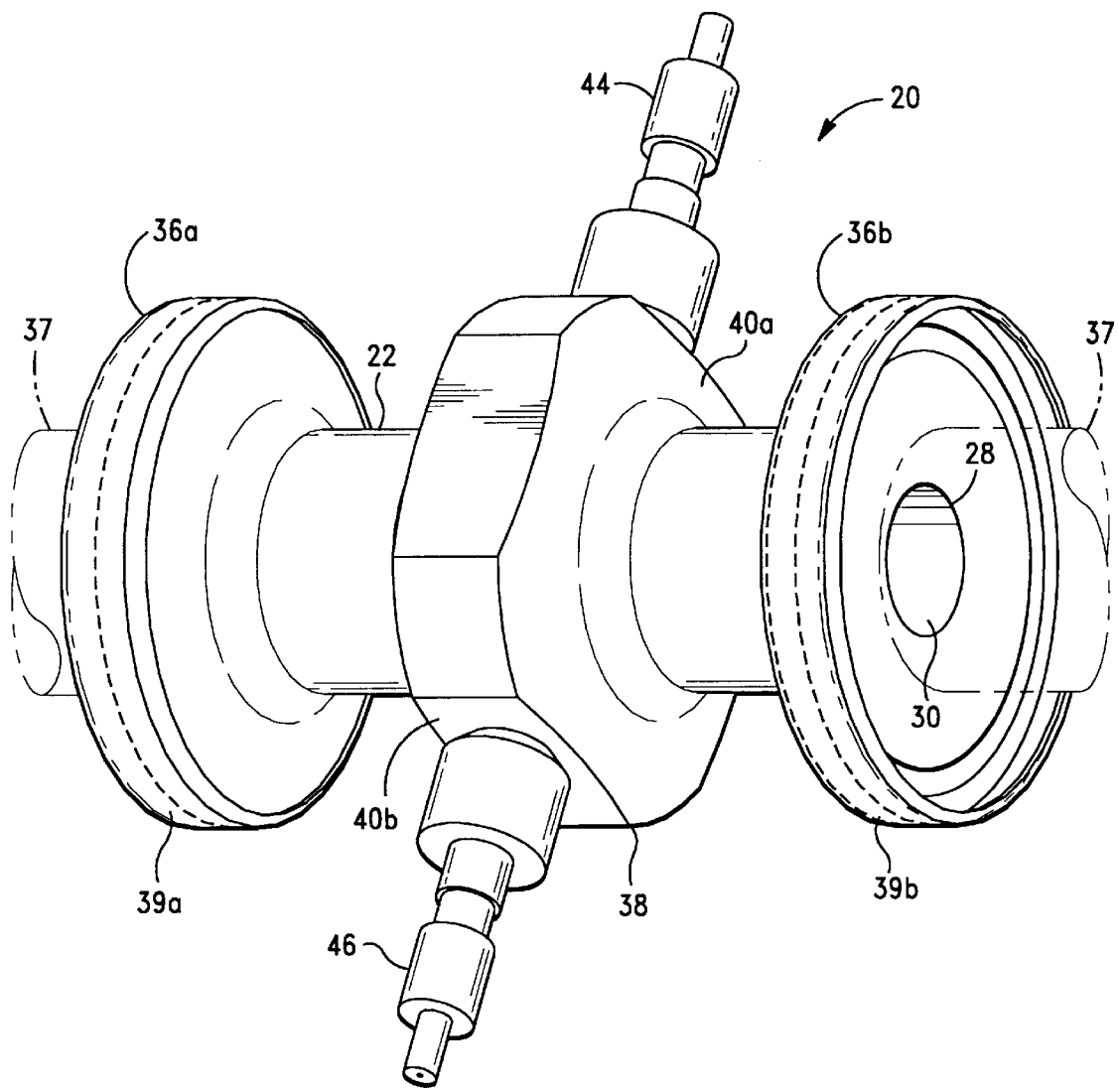
FIG. 2 is a perspective view of the sample flow cell and probe apparatus according to the invention.

Referring now to FIG. 2, there is shown the unique sample flow cell and probe apparatus of the invention, designated generally 20. The flow cell 20 includes a substantially cylindrical cell body 22 preferably constructed out of a suitable corrosion resistant material, such as stainless steel, titanium, or a non-metallic material, such as a high strength composite or polymeric material.

Figure 5:
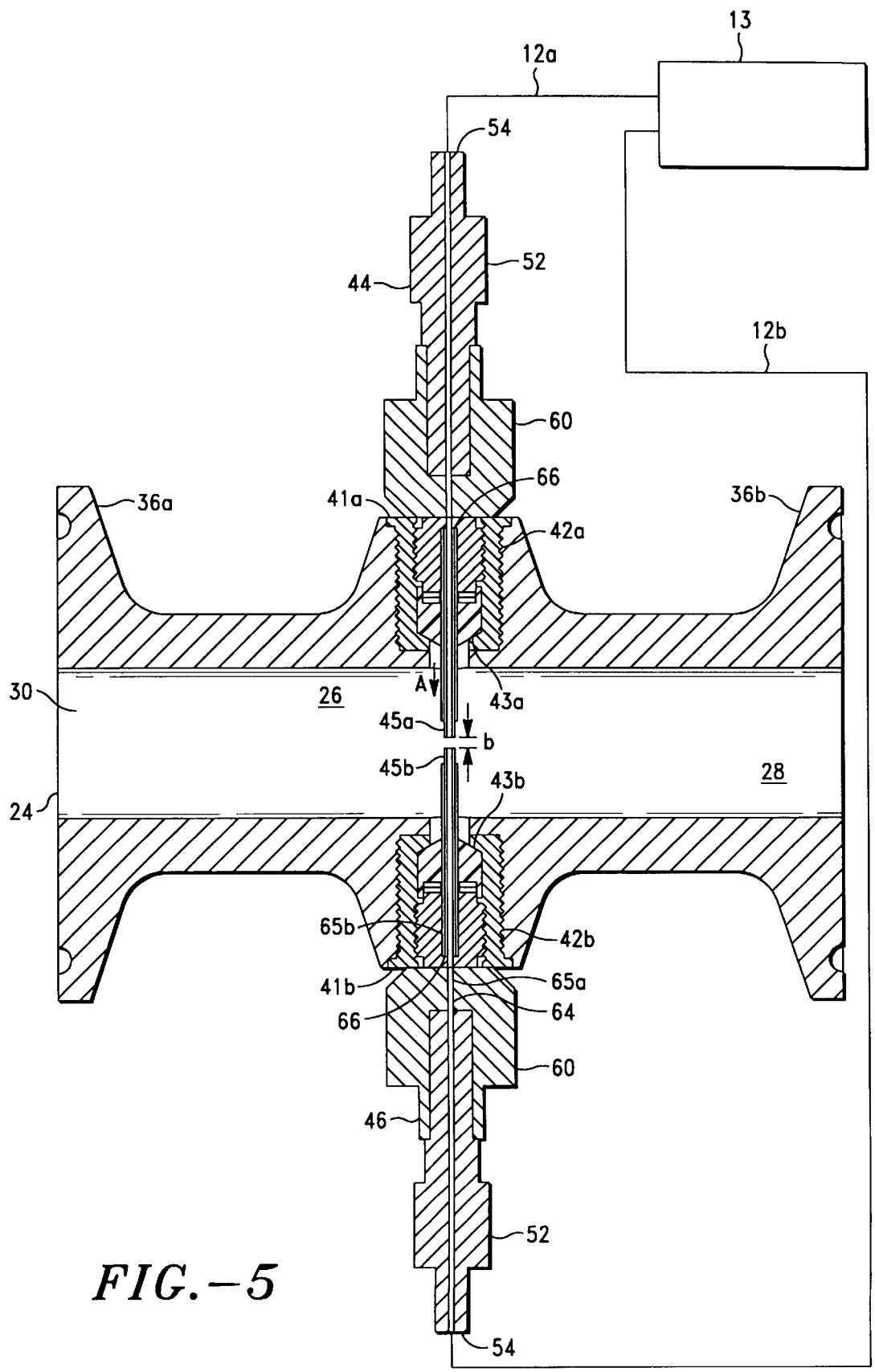
FIG. 5 is a sectional plan view of the sample flow cell and probe apparatus according to the invention.

The cell body 22 includes an inlet port 24, outlet port 28 and a cell chamber, designated generally 26, disposed therebetween (see FIG. 5). According to the invention, the inlet and outlet ports 24, 28 and chamber 26, define a flow passage 30, which, according to the invention, can have a diameter in the range of approximately 100 μm to 152.4 mm.

In a preferred embodiment of the invention, the cell body 22 also includes a pair of opposed, substantially cylindrical flange portions 36a, 36b adapted to sealably secure the flow cell 20 to the process control line (shown in phantom and designated generally 37) via conventional gasket and clamp assemblies (also shown in phantom and designated 39a, 39b, respectively). As illustrated in FIG. 2, the cell body 22 further includes a substantially cylindrical raised boss section 38 disposed proximate the center portion of the cell body 22. The boss section 38 includes at least one pair of opposed substantially planar optic member seats 40a, 40b (see FIG. 7). As discussed in detail below, the seats 40a, 40b are disposed on substantially parallel planes to position the optic members (or probes) 44, 46 of the invention.

The boss section 38 also includes a pair of opposed and generally coaxially aligned optic ports 42a, 42b (see FIG. 5). The optic ports 42a, 42b are designed and adapted to threadably receive the probe fittings 41a, 41b, discussed below.

As will be appreciated by one having ordinary skill in the art, the cell body 22 can comprise various sizes and configurations; provided, the cell body 22 includes the flow passage 30 described above and the means for positioning the optic members 44, 46, discussed in detail below.

Figure 4:
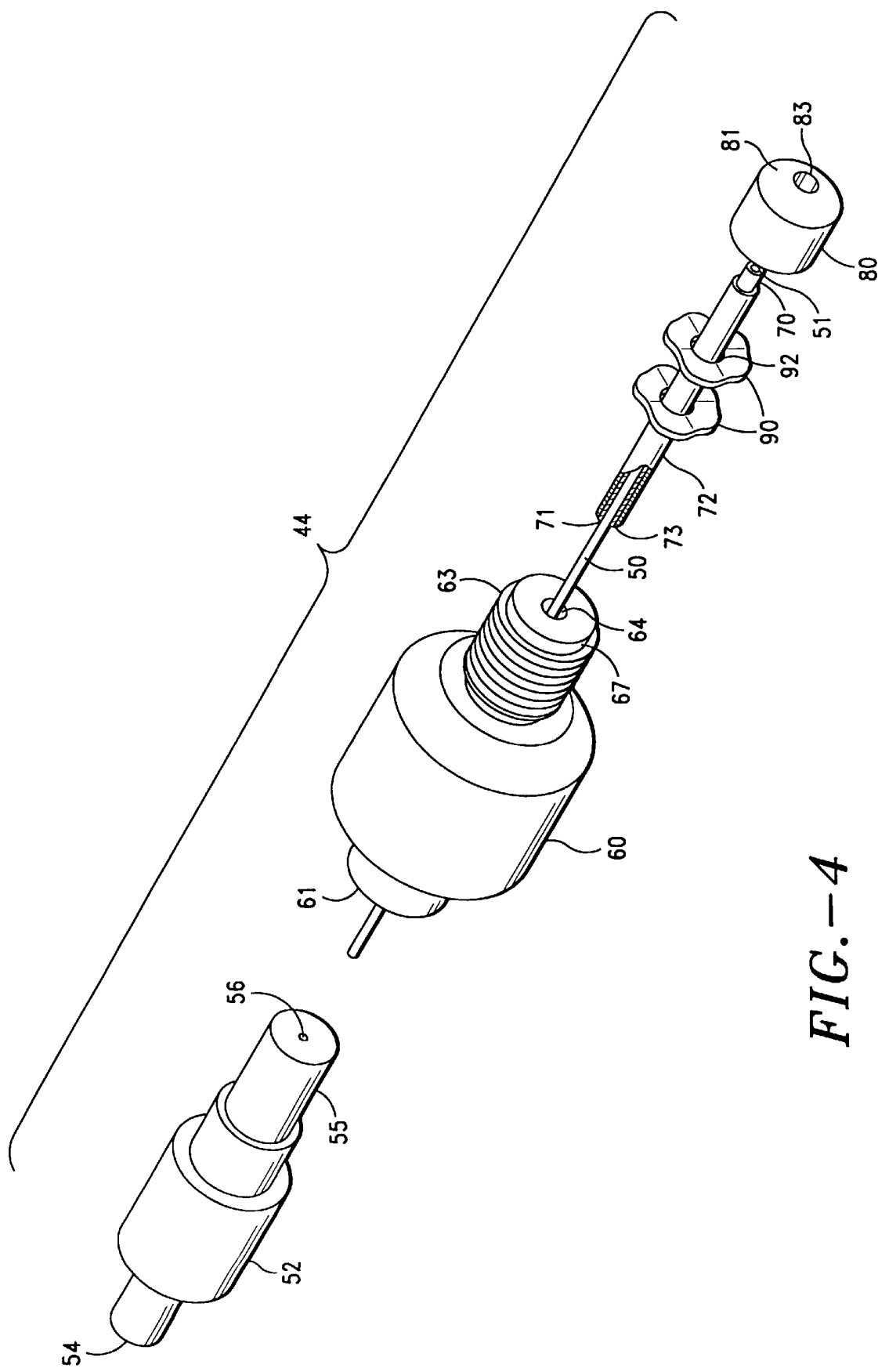
FIG. 4 is an exploded perspective view of a probe member according to the invention.

Referring now to FIG. 4, there is shown the preferred optic member 44 of the invention. For simplicity, only optic member 44 will be described in detail. However, it is to be understood that optic member 46 is similarly constructed and the description of optic member 44 is equally applicable to each member 44, 46.

As illustrated in FIG. 4, the optic member 44 includes light transmission means (in the case of member 46, light detection means) or optic cable 50, which, in a preferred embodiment of the invention, comprises a single optic fiber. In additional envisioned embodiments of the invention, not shown, a plurality or bundle of fibers are employed.

Figure 3:
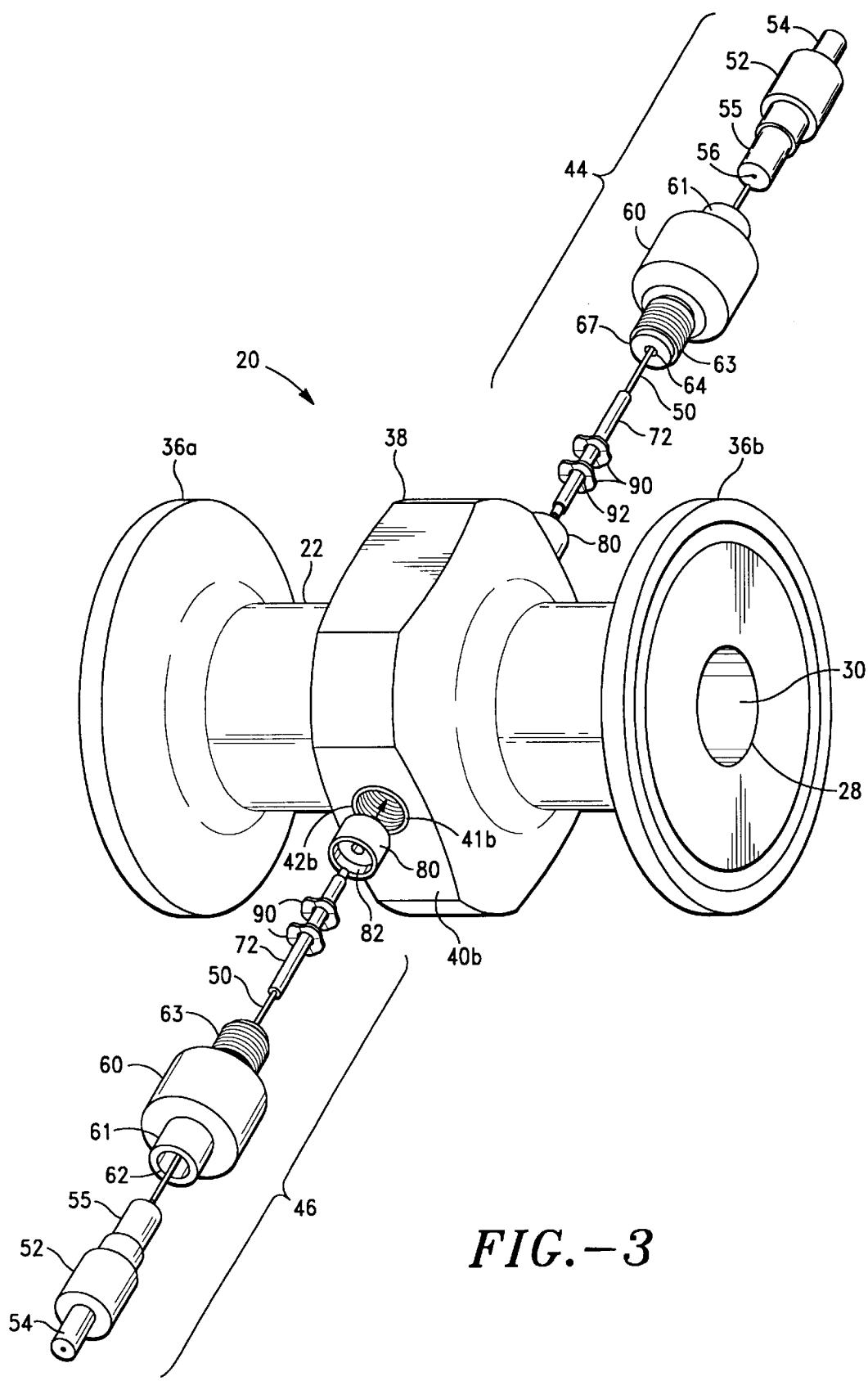
FIG. 3 is an exploded perspective view of the sample flow cell and probe apparatus according to the invention.

The optic member 44 further includes a cable guide 52, a probe body 60, first and second cable sleeves 70, 72 and a gasket plug 80. As illustrated in FIGS. 3 and 4, the cable guide 52 is preferably an elongated member having a substantially circular cross-section. According to the invention, the cable guide 52 includes an analyzer connector section 54 adapted to receive the control means 13 leads (not shown), a probe body engagement portion 55 adapted to slideably engage the probe body guide recess 62, and a cable guide lumen 56 adapted to receive and secure the optic cable 50 therein.

The probe body 60 similarly has a substantially circular cross-section. The probe body 60 includes a probe body cable lumen 64 having a first section 65a adapted to receive the optic cable 50, a second section 65b adapted to slideably receive the cable 50 and first and second cable sleeves 70, 72, and a sleeve seat 66 adapted to position the cable sleeves 70, 72 in the cable lumen 64 (see FIG. 5).

The probe body 60 further includes a cable guide connector section 61 having the above referenced probe body guide recess 62 disposed therein, a gasket plug seat 67, and preferably a threaded male connector section 63 adapted to threadably engage a respective one of the probe fittings 41a, 41b. In additional embodiments of the invention, not shown, each of the probe fittings 41a, 41b includes the male portion and the probe body 60 includes a female portion that is adapted to threadably engage the probe fitting.

According to the invention, the cable guide 52 and probe body 60 can be constructed out of various light weight, high strength materials, such as stainless steel, aluminum, titanium and/or high strength polymeric or composite materials. In a preferred embodiment of the invention, the cable guide 52 and probe body 60 are constructed out of stainless steel.

As will be appreciated by one having ordinary skill in the art, various configurations and sizes of the probe body 60 and cable guide 52 may be employed within the scope of the invention. The probe body 60 and cable guide 52 can also comprise an integral unit.

As illustrated in FIGS. 4 and 5, the optic member 44 includes a gasket plug 80 adapted to seal the optic ports 42a, 42b when the optic members 44, 46 are threadably engaged to the probe fittings 41a, 41b. As illustrated in FIGS. 3 and 4, the gasket plug 80 has a substantially circular cross section that is correspondingly similar to and preferably slightly less than the inside diameter of the probe fittings 41a, 41b, a tapered face section 81 adapted to engage the probe fitting seats 43a, 43b when the gasket plug 80 is positioned in a respective one of the probe fittings 41a, 41b, and a probe body recess 82 adapted to slideably receive the gasket plug seat 67. The gasket plug 80 further includes a gasket cable lumen 83 adapted to slideably (and preferably, sealably) receive the optic cable 50 and first and second cable sleeves 70, 72.

According to the invention, the gasket plug 80 can be constructed out of various materials, such as Teflon®, Klrez® and Neoprene®. In a preferred embodiment, the gasket plug 80 is constructed out of Teflon®.

As illustrated in FIG. 3, the optic member 44 also includes at least one, preferably two, conventional disk springs 90 that are disposed between the probe body 60 and the gasket plug 80. According to the invention, the disk springs 90 provide an additional sealing force (i.e., biasing the gasket plug 80 in an inward direction, denoted by Arrow A) when the probe member 44 is threadably engaged to the cell body 22 (see FIG. 5).

In a preferred embodiment of the invention, each disk spring 90 has an outer diameter that is slightly less than the diameter of the probe body recess 82. Each spring 90 further includes a spring lumen 92 adapted to slideably receive the cable 50 and first and second cable sleeves 70, 72.

Two key components of the optic member 44 are the first and second cable sleeves 70,72. According to the invention, the cable sleeves 70,72 are employed to protect and enhance the structural integrity (e.g., rigidity) of the optic cable 50.

As illustrated in FIGS. 4 and 5, the first (or inner) sleeve 70 is a tubular, elongated member having a first sleeve lumen 71 adapted to slideably receive the optic cable 50 therein. In preferred embodiment of the invention, the optic cable 50 is bonded to the first sleeve 70 by conventional means (e.g., epoxy).

The second (or outer) sleeve 72 is similarly a tubular elongated member having a second sleeve lumen 73 adapted to slideably receive the optic cable 50 and first sleeve 70 therein. In preferred embodiment of the invention, the second sleeve 72 is bonded to the first sleeve 70 by conventional means. The second sleeve 72 is also preferably bonded to the cable body 60 (i.e., in the second section 65b of probe body lumen 64).

The sleeves 70, 72 are preferably constructed out of a suitable corrosion resistant material, such as stainless steel or titanium. In a preferred embodiment of the invention, the sleeves 70, 72 are constructed out of stainless steel.

In additional envisioned embodiments of the invention, not shown, one sleeve is employed to protect and enhance the structural integrity of the optic cable 50. In addition to the above noted materials, the single sleeve can also be constructed out of various high strength, non-metallic materials and Nitinol® or other like materials.

In yet further additional embodiments of the invention, the optic cable tips 51 are coated with a fluropolymer or other like inorganic material. Applicants have particularly found that the application of a fluropolymer coating to the cable tips 51 substantially enhances the structural integrity of the optic cable 50 and its resistance to erosion, contamination and fracture.

Figure 7:
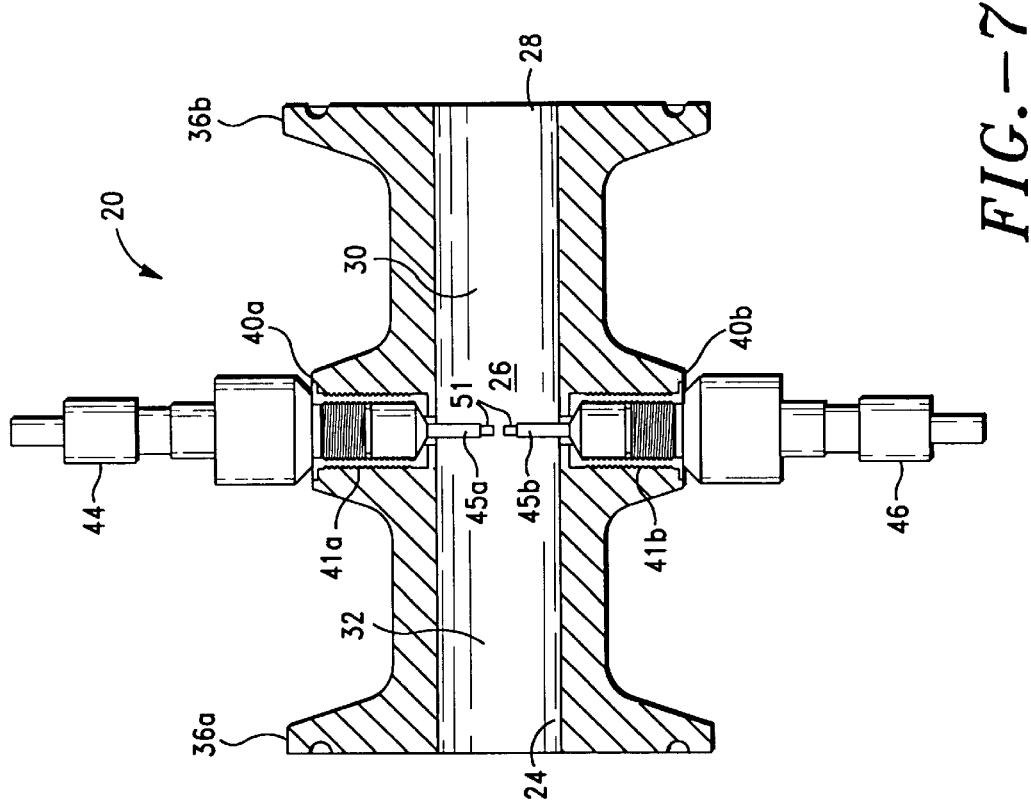
Figure 6:
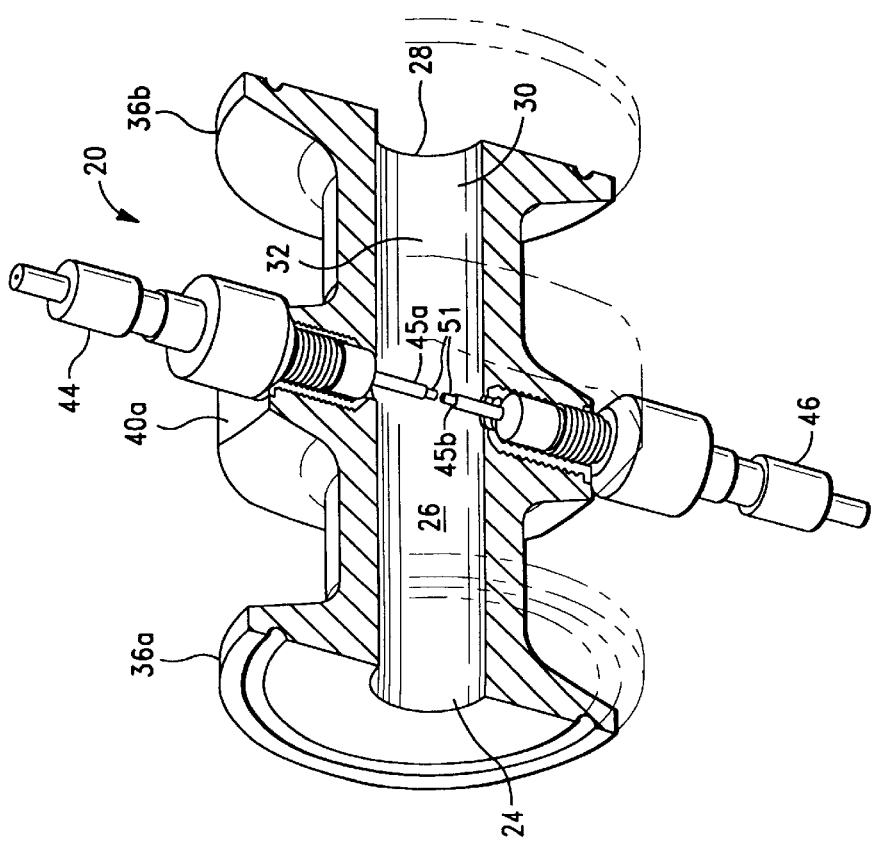
FIG. 6 is a partial section perspective view of the sample flow cell and probe apparatus according to the invention.

Referring now to FIGS. 6–8, there are shown partial section views of the sample flow cell and probe apparatus 20, illustrating the preferred position of the probe members 44, 46 on the cell body 22. Referring to FIG. 7, each probe member 44, 46 is threadably, substantially coaxially aligned and secured to the cell body 22 via the probe fittings 41a, 41b. According to the invention, when the probe members 44, 46 are in the noted positions—i.e., probe body seats (or faces) 68 abut against optic member seats 40a, 40b—, a path length (b) in the range of approximately 1 $\mu$m to 10 mm, more preferably, 20 $\mu$m to 1.0 mm is provided.

Referring now to FIG. 8, in a preferred embodiment of the invention, the probe members 44, 46 project into the cell chamber 26 such that the probe member ends 45a, 45b are and, hence, optic cable tips 51 disposed in a "region of reasonable flow", designated generally X. By the term "region of reasonable flow", as used herein, it is meant to mean a region within the cell chamber 26 wherein the flow rate of the sample is less than approximately 20%, more preferably, less than 40% of the maximum flow rate of the sample in the cell chamber 26. As will be appreciated by one having ordinary skill in the art, the "region of reasonable flow", as defined, will typically be exhibited proximate the flow channel wall.

Applicants have found that the noted position of the probe members 44, 46 reduces obstruction to the flow of the sample and significantly minimizes erosion and contamination of the cable tips 51.

As discussed in detail above, each optic member 44, 46 includes a cable guide 52 having an analyzer connector section 54 adapted to receive a respective one of the control means leads (i.e., 12a, 12b) to facilitate communication to and between the control means 13 and the optic members 44, 46. In the embodiment of the invention shown in FIG. 5, optic member 44 is operatively connected to the control means light source 14 and optic member 46 is operatively connected to the control means analyzer 15.

In operation, the light provided by the light source, which, according to the invention, can be in the range of 190 to 2500 nanometers, is transmitted into and through the cell chamber 26 by optic member 44. The emission (or emitted) light is detected by optic member 46, which communicates a signal representing the emission light to the control means analyzer 15.

As will be appreciated by one having ordinary skill in the art, various control means and/or analyzers can be employed within the scope of the invention to provide a given wavelength of light, compare the absorption spectrum of the emission light and control the spectroscopic analysis process, such as the analyzer disclosed in U.S. Pat. No. 4,664,522. In a preferred embodiment of the invention, the control means comprises a Carl Zeiss, MCS-521 fiber optic UV/VIS spectrophotometer equipped with a CLD-500 deuterium lamp.

According to the invention, the sample flow cell and probe apparatus 20 is preferably calibrated as follows:

Step 1—Seal one end of the cell body 22 with an end cap (not shown).

Step 2—Fill the flow channel 30 with water and obtain a transmitted energy spectrum (i.e., $I_o$ in Eq. 1).

Step 3—Fill the flow channel 30 with a prepared solution of potassium dichromate (having a certified absorbance) and obtain a sample absorbance spectrum (i.e., I in Eq. 1)

Step 4—Using the following equation, which is a derivation of Eq. 1 (i.e., Beer's Law), calculate the effective flow path length ($P_{fc}$)

$$P_{fc} = P_c \times A_{fc}/A_c \qquad \text{Eq.2}$$

where:

$P_c$=Path length of cuvette $A_{fc}$=Absorbance of potassium dichromate in the flow cell.

$A_c$=Absorbance of potassium dichromate in the cuvette (i.e., standard).

According to the method of the invention, spectroscopic analysis of a sample (i.e., flowable material) is accomplished as follows:

The sample flow cell 20 is initially calibrated as discussed above. After the calibration step, the sample is introduced into the flow passage 30.

The absorption spectra of the sample is then measured and analyzed by the control means 13 of the invention. Such analysis includes a comparison of the detected spectra against at least one standard spectrum, confirmation of constituents in the sample and a determination of the concentration of each constituent in the sample.

From the foregoing description, one of ordinary skill in the art can easily ascertain that the present invention provides numerous advantages over prior art optic-based systems. A key advantage is the provision of a path length in the range of 1 $\mu$m to 10 mm.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An apparatus for in-situ analysis of a flowable material, comprising:

a flow cell having a flow passage and means for introducing said flowable material into said flow passage for flowing therethrough, said flow cell including a cell chamber in communication with said flow passage, said cell chamber including a region of reasonable flow; said region of reasonable flow having a flow rate less than approximately 20% of the maximum flow rate through said cell chamber;

a first probe for transmitting light of a given wavelength into said cell chamber, said first probe including a first optic cable member having first and second ends, said first end of said first optic cable member being disposed in said region of reasonable flow;

a second probe for detecting emission light from said flowable material, said second probe including a second optic cable member having first and second ends, said first end of said second optic cable member being disposed in said region of reasonable flow;

said first and second probes having a path length in the range of approximately 20 $\mu$m to 1 mm; and control means in communication with said second ends of said first and second optic cable members for providing said light to said first end of said first optic cable member and analyzing said emission light detected by said first end of said second optic cable member.

2. An apparatus for in-situ analysis of a flowable material, comprising:

a flow cell having a flow passage and means for introducing said flowable material into said flow passage for flowing therethrough, said flow cell including a cell chamber in communication with said flow passage, said cell chamber having a cell chamber wall and including a region of reasonable flow; said region of reasonable flow being disposed proximate said cell chamber wall;

said flow cell further including a first probe bore having a first probe seat disposed proximate one end thereof and a second probe bore having a second probe seat disposed proximate one end thereof;

a first probe for transmitting light of a given wavelength into said cell chamber, said first probe including a first optic cable member having first and second ends, said first end of said first optic cable member being disposed in said region of reasonable flow, said first probe being supported in said first probe bore;

a second probe for detecting emission light from said flowable material, said second probe including a second optic cable member having first and second ends, said first end of said second optic cable member being disposed in said region of reasonable flow, said second probe being supported in said second probe bore;

said first probe seat including first positioning means for positioning said first probe in a first predetermined position relative to said second probe and said second probe seat including second positioning means for positioning said second probe in a second predetermined position relative to said first probe whereby when said first probe is in said first predetermined position and said second probe is in said second predetermined position said first and second probes have a path length in the range of approximately 20 μm to 1 mm; and control means in communication with said first and second probes for providing said light to said first probe and analyzing said emission light detected by said second probe.

3. The apparatus of claim 2, wherein said first and second probe bores have substantially coincident axes and are disposed substantially perpendicular to said flow passage.

4. The apparatus of claim 2, wherein said first and second probes include sealing means for sealing said first and second probe bores.

5. The apparatus of claim 2, wherein said first ends of said first and second optic cable members are coated with a fluropolymer.

6. A method for in-situ analysis of a flowable material having a plurality of constituents, comprising the steps of:

providing a flow cell having a flow passage therein, said flow cell including a cell chamber in communication with said flow passage having a region of reasonable flow, a first probe for transmitting light of a given wavelength into said cell chamber, said first probe including a first optic cable member having first and second ends, said first end of said first optic cable member being disposed in said region of reasonable flow, a second probe for detecting emission light from said flowable material, said second probe means including a second optic cable member having first and second ends, said first end of said second optic cable member being disposed in said region of reasonable flow, said first and second probes having a path length in the range of approximately 20 μm to 1 mm;

introducing a first material into said flow passage;

measuring the absorption spectrum of said first material to obtain a transmitted energy spectrum by passing at least said given wavelength of light through said first material;

introducing a second material into said flow passage;

measuring the absorption spectrum of said second material by passing at least said given wavelength of light through said second material;

determining the effective flow path length ($P_{fc}$) by the following relationship, $$P_{fc} = P_c \times A_{fc}/A_c$$

where:

$P_c$=Path length of a cuvette, $A_{fc}$=Absorbance of said second material in said flow cell, $A_c$=Absorbance of said second material in said cuvette;

introducing said flowable material into said flow passage;

measuring the absorption spectrum of said flowable material by passing at least said given wavelength of light through said flowable material;

confirming the presence of at least one constituent in said flowable material; and determining the concentration of at least one constituent in said flowable material.

7. The method of claim 6, wherein said first material comprises water.

8. The method of claim 6, wherein said second material comprises potassium dichromate.

* * * * *

UNITED STATES PATENT AND TRADEMARK OFFICE
CERTIFICATE OF CORRECTION

PATENT NO. : 6,515,748 B2  
DATED : February 4, 2003  
INVENTOR(S) : Walker, Dwight Sherod et al.

It is certified that error appears in the above-identified patent and that said Letters Patent is hereby corrected as shown below:

Column 4,
Line 14, "= Molar" should read -- α = Molar --
Line 19, "product of bc" should read -- product of α bc --

Signed and Sealed this

Eleventh Day of November, 2003

JAMES E. ROGAN
*Director of the United States Patent and Trademark Office*